United States Patent
Lee et al.

(10) Patent No.: US 10,920,257 B2
(45) Date of Patent: Feb. 16, 2021

(54) METHOD OF PRODUCING HIGH PURITY D-PSICOSE

(71) Applicant: CJ CHEILJEDANG CORPORATION, Seoul (KR)

(72) Inventors: Joo Hang Lee, Ansan (KR); Min Hoe Kim, Incheon (KR); Seong Bo Kim, Seongnam (KR); Seung Won Park, Yongin (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 163 days.

(21) Appl. No.: 15/776,930

(22) PCT Filed: Apr. 12, 2016

(86) PCT No.: PCT/KR2016/003843
§ 371 (c)(1),
(2) Date: May 17, 2018

(87) PCT Pub. No.: WO2017/150766
PCT Pub. Date: Sep. 8, 2017

(65) Prior Publication Data
US 2018/0327796 A1    Nov. 15, 2018

(30) Foreign Application Priority Data
Feb. 29, 2016   (KR) .......................... 10-2016-0024193

(51) Int. Cl.
*C12P 19/24*   (2006.01)
*C12P 19/02*   (2006.01)
(Continued)

(52) U.S. Cl.
CPC ................ *C12P 19/24* (2013.01); *C12N 9/90* (2013.01); *C12P 19/02* (2013.01); *A23L 27/33* (2016.08);
(Continued)

(58) Field of Classification Search
CPC ............ C12P 19/24; C12P 19/02; C12N 9/90
(Continued)

(56) References Cited

U.S. PATENT DOCUMENTS 4,133,375 A † 1/1979 Ducasse
5,523,064 A * 6/1996 Schranz ............... B01D 9/0013
                                                        422/245.1
(Continued)

FOREIGN PATENT DOCUMENTS

CN         101177672 A      5/2008
CN         103333935 A     10/2013
(Continued)

OTHER PUBLICATIONS

Office Action from Australian Patent Office for Application No. 2016395363, dated Nov. 7, 2018.
(Continued)

*Primary Examiner* — Yong D Pak

(57) ABSTRACT

Disclosed herein is a method of producing D-psicose. The method of producing D-psicose includes subjecting D-fructose to D-psicose epimerization to produce a D-psicose-containing solution, subjecting the D-psicose-containing solution to first cooling and ion purification, subjecting the purified D-psicose-containing solution to first concentration and second cooling, subjecting the D-psicose-containing solution, which has been subjected to first concentration and second cooling, to chromatography to obtain a D-fructose-containing mother liquor and a D-psicose-containing separated solution, and subjecting the D-psicose-containing separated solution to second concentration and third cooling to obtain D-psicose crystals, wherein the D-fructose-containing mother liquor produced by chromatography is reused in the D-psicose epimerization.

16 Claims, 7 Drawing Sheets

(51) Int. Cl.
*C12N 9/90* (2006.01)
*B01D 15/36* (2006.01)
*A23L 27/30* (2016.01)
*C13K 13/00* (2006.01)

(52) U.S. Cl.
CPC ........ *A23V 2002/00* (2013.01); *B01D 15/361* (2013.01); *C13K 13/007* (2013.01)

(58) Field of Classification Search
USPC .......................................... 435/94, 105, 233
See application file for complete search history.

(56) References Cited

U.S. PATENT DOCUMENTS

| | | | | |
|---|---|---|---|---|
| 8,524,888 | B2 * | 9/2013 | Lee | .......................... C07H 3/02 |
| | | | | 536/127 |
| 8,735,106 | B2 * | 5/2014 | Hong | ...................... C12P 19/24 |
| | | | | 435/105 |
| 10,246,476 | B2 * | 4/2019 | Kim | ...................... B01D 15/185 |
| 2011/0237790 | A1 † | 9/2011 | Lee | |
| 2012/0094940 | A1 † | 4/2012 | Takamine | |

FOREIGN PATENT DOCUMENTS

| | | | |
|---|---|---|---|
| JP | 2005-263670 A † | 9/2005 | |
| JP | 2005263670 A | 9/2005 | |
| JP | 2011206054 A | 10/2011 | |
| JP | 2013501519 A | 1/2013 | |
| KR | 10-2009-0118465 * | 12/2009 | |
| KR | 10-2011-0035805 A | 4/2011 | |
| KR | 10-2011-0108185 A | 10/2011 | |
| KR | 10-1203856 B1 | 11/2012 | |
| KR | 10-1455759 B1 | 10/2014 | |
| KR | 10-2016-0119331 A | 10/2016 | |
| RU | 2487884 C1 | 7/2013 | |
| WO | 2011040708 A2 | 4/2011 | |
| WO | 2011119004 A2 | 9/2011 | |
| WO | 2014196811 A1 | 12/2014 | |

OTHER PUBLICATIONS

Van Duc Long Nguyen et al., "Separation of D-psicose and D-fructose using simulated moving bed chromatography", Journal of Separation Science, 2009, pp. 1987-1995, vol. 32, Wiley-VCH Verlag GmbH & Co.
Ikuko Tsukamoto et al., "Intestinal absorption, organ distribution, and urinary excretion of the rare sugar D-psicose," Drug Design, Development and Therapy, 2014, pp. 1955-1964, vol. 8, Dovepress.
Tatsuhiro Matsuo et. al., "Dietary D-psicose, a C-3 epimer of D-fructose, suppresses the activity of hepatic lipogenic enzymes in rats", Asia Pacific Journal of Clinical Nutrition, 2001, pp. 233-237, vol. 10, No. 3.
T Matsuo et al., D-Psicose, a rare sugar that provides no energy and additionally beneficial effects for clinical nutrition, Asia Pacific Journal of Clinical Nutrition, 2004, pp. S127, vol. 13 (Suppl).
International Search Report for PCT/KR2016/003843 filed on Apr. 12, 2016.
N. Wagner et al., "Model-based cost optimization of a reaction-separation integrated process for the enzymatic production of the rare sugar D-psicose at elevated temperatures", Chemical Engineering Science 137, 2015, pp. 423-435, Bioprocess Laboratory, Department of Biosystems Science and Engineering, ETH Zurich, Switzerland, www.elsevier.com/locate/ces.
N. Wagner et al., "Multi-objective optimization for the economic production of D-psicose using simulated moving bed chromatography", Journal of Chromatography A 1398, 2015, pp. 47-56, Bioprocess Laboratory, Department of Biosystems Science and Engineering, ETH Zurich, Switzerland, www.elsevier.com/locate/chroma.
Hiromichi Itoh, "Preparation of D-Psicose from D-Fructose by Immobilized D-Tagatose 3-Epimerase", pp. 101-103, Journal of Fermentation and Bioengineering (vol. 80 No. 1), published 1995, the Society for Biotechnology, Japan.†

* cited by examiner
† cited by third party

METHOD OF PRODUCING HIGH PURITY D-PSICOSE

CROSS-REFERENCE TO RELATED APPLICATIONS

The present specification is a U.S. National Stage of International Patent Application No. PCT/KR2016/003843 filed Apr. 12, 2016, which claims priority to and the benefit of Korean Patent Application No. 10-2016-0024193 filed in the Korean Intellectual Property Office on Feb. 29, 2016, the entire contents of which are incorporated herein by reference.

BACKGROUND

1. Technical Field

The present invention relates to a method of producing D-psicose, and more particularly, to a method of producing high purity D-psicose with high yield without heat deformation during production.

2. Description of the Related Art

It has been reported that D-psicose is a sweetener that is scarcely metabolized in the body unlike fructose or sucrose, has substantially no calories, and has little effect on body weight gain because it inhibits the formation of body fat (Matsuo, T. et. Al. *Asia Pac. J. Clin. Untr.*, 10, 233-237, 2001; Matsuo, T. and K. Izumori, *Asia Pac. J. Clin. Nutri*, 13, S127, 2004).

Recently, the present inventors have reported a method for economically producing D-psicose by isomerizing D-glucose to D-fructose, followed by reacting the resultant D-fructose with immobilized cells capable of producing D-psicose epimerase (Korean Patent Application No. 10-2009-0118465).

Since the reaction solutions containing D-psicose produced by the enzymatic reaction are low purity products containing D-psicose with solids content of about 20% (w/w) to about 30% (w/w), it is necessary to purify D-psicose through continuous chromatography in order to produce high purity D-psicose crystals having a purity of 98% (w/w) or more.

Since the conversion rate for enzyme reaction of D-psicose produced from D-fructose by the above method is 20% (w/w) to 30% (w/w), the reaction exhibits the process flow in which the amount of mother liquor generated in the process, namely the amount of D-fructose mother liquor separated from continuous chromatography and the mother liquor separated from crystallization is higher than the amount of D-psicose produced. As a result, reduction in the produced amount of D-psicose leads to increase in manufacturing cost which in turn increases production costs, causing problems in view of uneconomical industrial production.

Accordingly, in order to inhibit the increase of manufacturing cost due to low yield, there is a need for a method capable of producing high purity D-psicose with high yield.

BRIEF SUMMARY

Embodiments of the present invention provide a method of producing high purity D-psicose in high yield.

In accordance with one embodiment of the present invention, a method of producing D-psicose includes: subjecting D-fructose to D-psicose epimerization to produce a D-psicose containing solution; subjecting the D-psicose-containing solution to first cooling and ion purification; subjecting the purified D-psicose-containing solution to first concentration and second cooling; subjecting the D-psicose-containing solution, which has been subjected to first concentration and second cooling, to chromatography to obtain a D-fructose-containing mother liquor and a D-psicose-containing separated solution; and subjecting the D-psicose-containing separated solution to second concentration and third cooling to obtain D-psicose crystals, wherein the D-fructose-containing mother liquor produced by chromatography is reused in the D-psicose epimerization.

In accordance with another embodiment of the present invention, a method of producing D-psicose includes: subjecting D-fructose to D-psicose epimerization to produce a D-psicose-containing solution; subjecting the D-psicose-containing solution to first cooling and ion purification; subjecting the purified D-psicose-containing solution to first concentration and second cooling; subjecting the D-psicose-containing solution, which has been subjected to first concentration and second cooling, to chromatography to obtain a D-fructose-containing mother liquor and a D-psicose-containing separated solution; and subjecting the D-psicose-containing separated solution to second concentration and third cooling to obtain D-psicose crystals, wherein the D-fructose-containing mother liquor produced by chromatography is reused in the D-psicose epimerization, and wherein the mother liquor produced by the D-psicose crystallization is reused in any of the first cooling and ion purification, the first concentration and second cooling, and chromatography.

In the one embodiment or the other embodiment, the method may further include cooling the D-fructose-containing mother liquor produced by the chromatography or the mother liquor produced by the D-psicose crystallization to 25° C. to 45° C., specifically 30° C. to 40° C. before the D-fructose-containing mother liquor produced by the chromatography or the mother liquor produced by the D-psicose crystallization is reused. The chromatography may be, for example, continuous chromatography.

In the one embodiment or the other embodiment, the first cooling and the third cooling may refer to a process of reducing the solution temperature or ambient temperature to 25° C. to 45° C., specifically 30° C. to 40° C., and the second cooling may refer to a process of reducing the solution temperature or ambient temperature to 45° C. to 65° C., specifically 50° C. to 60° C.

In the one embodiment or the other embodiment, the first concentration refers to a process of concentrating the purified D-psicose-containing solution to have a D-psicose concentration of 50 brix to 70 brix. The second concentration refers to a process of concentrating D-psicose in the separated solution to have a concentration of 75 brix or more, for example, 80 brix or more.

In the one embodiment or the other embodiment, as the D-fructose-containing mother liquor produced by chromatography, a D-fructose-containing fraction having a purity of 70% (w/w) or more may be used. As the mother liquor produced by D-psicose crystallization, a D-psicose-containing fraction having a purity of 90% (w/w) or more may be used.

In the one embodiment or the other embodiment, the D-psicose epimerization may include epimerization at a temperature of 40° C. to 70° C., specifically, 40° C. to 60° C., more specifically 40° C. to 50° C. in the presence of D-psicose epimerase, variants thereof, strains capable of producing the enzyme or cultures thereof.

In the one embodiment or the other embodiment, the ion purification may be performed using a strongly acidic cation exchange resin and/or a weakly basic anion exchange resin.

In the one embodiment or the other embodiment, the D-psicose-containing separated solution may contain D-psicose in an amount of 93% (w/w) or more, specifically 95% (w/w) or more.

In the one embodiment or the other embodiment, the first to third cooling may be heat exchange cooling. Advantageously, heat exchange cooling provides a wide heat transfer area and fast heat exchange due to occurrence of turbulent flow of fluids, prevents scale formation to provide little reduction in functions, thereby providing high economic feasibility.

In the one embodiment or the other embodiment, the obtained D-psicose crystals may have a purity of 95% (w/w) or more, more specifically 99% (w/w) or more.

In the one embodiment or the other embodiment, the D-psicose crystals prepared by the method as set forth above may have a yield of 75% or more, specifically 85% or more.

In another embodiment, the method of producing D-psicose provides D-psicose having a purity of 99% (w/w) or more.

The method of producing D-psicose according to embodiments of the present invention can prevent heat deformation of D-psicose and enables production of D-psicose with high yield through a stabilized process.

Further, the method of producing D-psicose according to embodiments of the present invention harvests a D-fructose-containing mother liquor produced by chromatography and/or mother liquor produced by D-psicose crystallization, which in turn is reused in D-psicose epimerization, first cooling and ion purification, first concentration and second cooling, or chromatography, thereby facilitating stable separation of D-psicose through chromatography after a long period of recirculation, and ensuring production of D-psicose with high yield.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Figure 1:
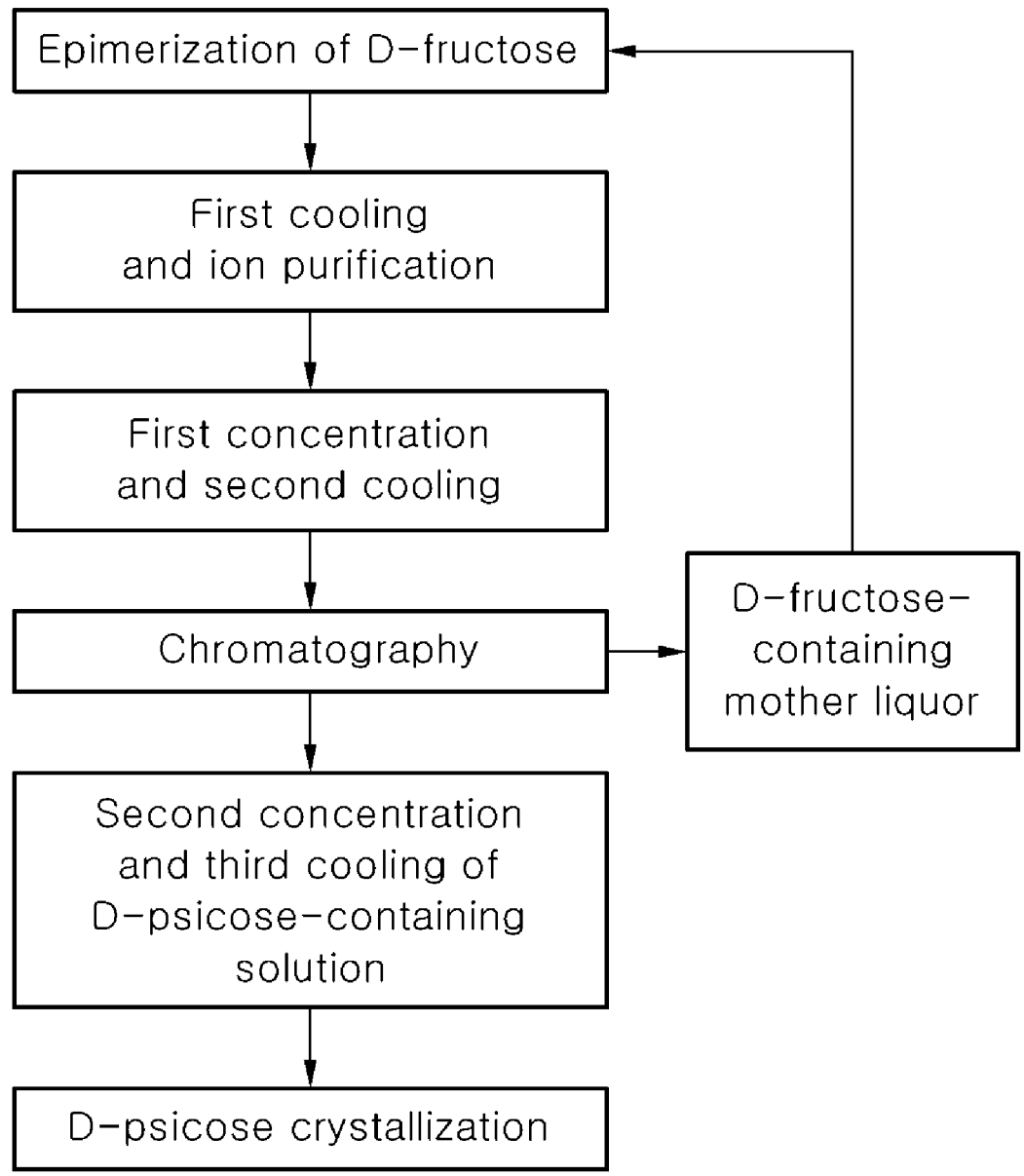
FIG. 1 is a schematic view depicting a method of producing D-psicose according to one embodiment of the present invention.
Figure 2:
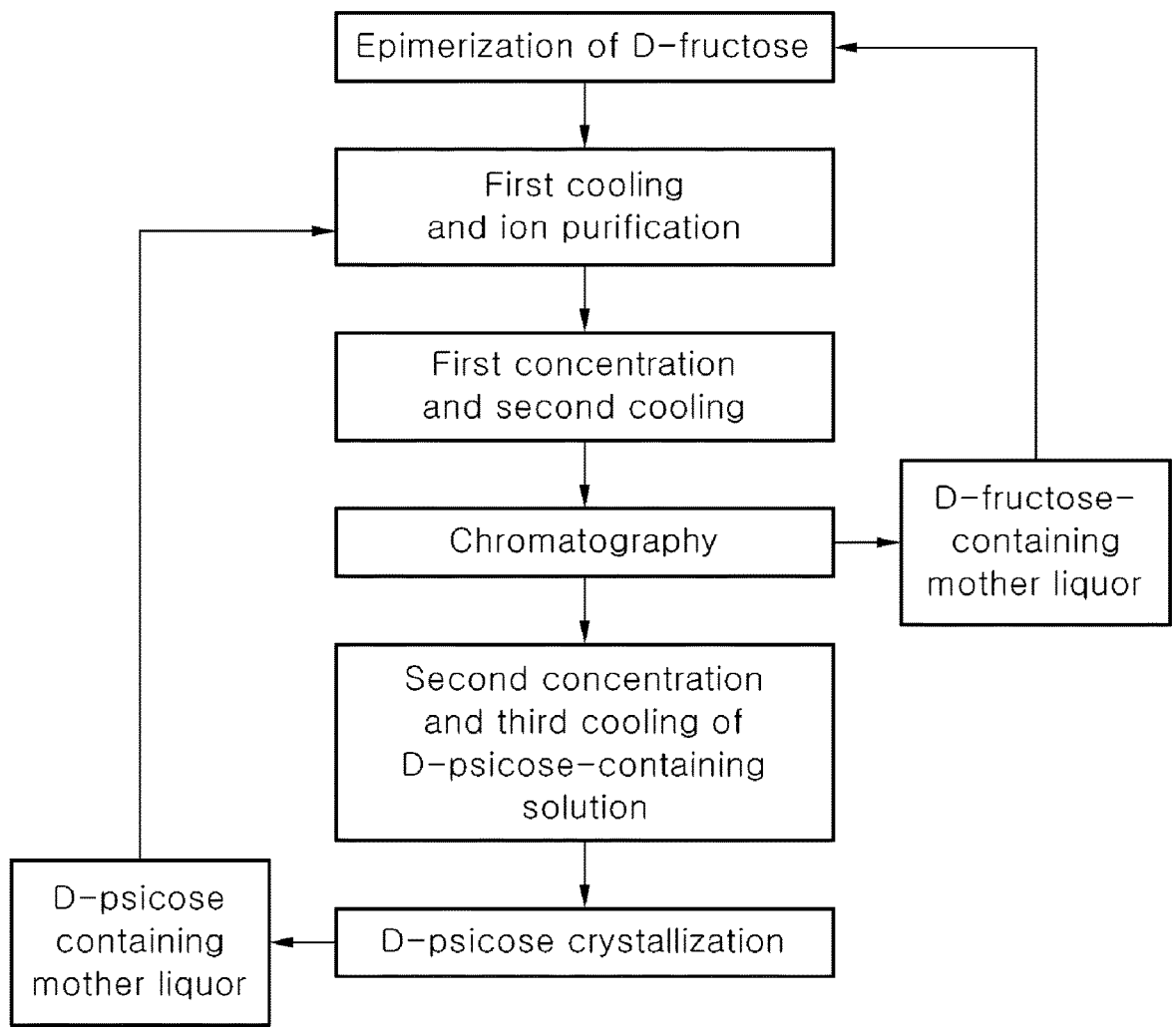
FIG. 2 is a schematic view depicting a method of producing D-psicose according to another embodiment of the present invention.

Hereinafter, embodiments of the present invention will be described in more detail. Descriptions of details apparent to those skilled in the art having ordinary knowledge in this technical field or relevant field will be omitted herein.

In one embodiment of the present invention, a method of producing D-psicose includes: subjecting D-fructose to D-psicose epimerization to produce a D-psicose-containing solution; subjecting the D-psicose-containing solution to first cooling and ion purification; subjecting the purified D-psicose-containing solution to first concentration and second cooling; subjecting the D-psicose-containing solution, which has been subjected to first concentration and second cooling, to chromatography to obtain a D-fructose-containing mother liquor and a D-psicose-containing separated solution; and subjecting the D-psicose-containing separated solution to second concentration and third cooling to obtain D-psicose crystals, wherein the D-fructose-containing mother liquor produced by chromatography is reused in the D-psicose epimerization.

In another embodiment of the present invention, a method of producing D-psicose includes: subjecting D-fructose to D-psicose epimerization to produce a D-psicose-containing solution; subjecting the D-psicose-containing solution to first cooling and ion purification; subjecting the purified D-psicose-containing solution to first concentration and second cooling; subjecting the D-psicose-containing solution, which has been subjected to first concentration and second cooling, to chromatography to obtain a D-fructose-containing mother liquor and a D-psicose-containing separated solution; subjecting the D-psicose-containing separated solution to second concentration and third cooling to obtain D-psicose crystals, wherein the D-fructose-containing mother liquor produced by chromatography is reused in the D-psicose epimerization, and wherein the mother liquor produced through the D-psicose crystallization is reused in any of the first cooling and ion purification, first concentration and second cooling, and chromatography.

In the method according to the present invention, the D-fructose-containing mother liquor produced by chromatography or the mother liquor produced through the D-psicose crystallization is reused in any of the D-psicose epimerization, the first cooling and ion purification, the first concentration and second cooling, and chromatography, and thus can produce D-psicose with high yield, thereby improving production efficiency while reducing production costs.

First, D-fructose used as a substrate for epimerization may be used in a concentration of 30 brix (%) to 50 brix (%) and may be dissolved in water at a temperature of 30° C. to 40° C. in use. Alternatively, D-fructose may be mixed with the D-fructose-containing mother liquor produced by chromatography and used in a concentration of 30 brix (%) to 50 brix (%) at a temperature of 30° C. to 40° C. Herein, as the D-fructose-containing mother liquor produced by chromatography, a D-fructose-containing fraction having a purity of 70% (w/w) or more, specifically 75% (w/w) or more may be used.

D-psicose epimerization refers to a process of producing D-psicose through epimerization of D-fructose in the presence of D-psicose epimerase, variants thereof, strains capable of producing the enzyme or cultures thereof. The D-psicose epimerase according to the present invention may include enzymes or variants thereof derived from various donor microorganisms such as *Agrobacterium tumefaciens*, *Flavonifractor plauti*, and *Clostridium hylemonae*. The strains for transformation may include *Escherichia coli* or genus *Corynebacterium*, genus *Bacillus*, and genus *Aspergillus*, without being limited thereto. The strains transformed by *Escherichia coli* may include, for example, BL21(DE3)/pET24-ATPE [Korean Patent Publication No. 10-2011-0035805A], BL21(DE3)/pET24-ATPE-2 [Korean Patent No. 10-1203856]. The strain of genus *Corynebacterium* may include *Corynebacterium glutamicum* ATCC13032/pCJ-1-ATPE [Accession number KCCM11046 disclosed in Korean Patent Publication No. 10-2011-0035805A], *Corynebacte-*

*rium glutamicum* ATCC13032/pFIS-1-ATPE-2 [Accession number KCCM11204P disclosed in Korean Patent No. 10-1203856], *Corynebacterium glutamicum* CJ KY [Accession number KCCM11403P disclosed in Korean Patent No. 10-1455759], *Corynebacterium glutamicum* ATCC13032/pFIS-2-ATPE-2 [Accession number KCCM11678P disclosed in Korean Patent Publication No. 10-2015-0047111A], and the like.

In one embodiment, epimerization may be performed by immobilizing D-psicose epimerase, variants thereof, strains capable of producing the enzyme or cultures thereof at a carrier, for example, sodium alginate, filling isomerization equipment, for example, a column, with the immobilized enzyme, and supplying a D-fructose-containing solution to the filled column. The temperature in the equipment may be maintained at 40° C. to 70° C., for example, at 40° C. to 55° C., for epimerization. The temperature of the D-fructose-containing solution supplied may be, for example, increased to 40° C. to 60° C., for example 50° C., at a heating rate of 5° C. to 20° C. per hour through a heat exchanger such that SV [Space Velocity: flow rate (L)/hour (Hr)/resin amounts (L)] becomes 0.5 to 3. D-psicose produced by the epimerization can have a purity of about 15% (w/w) to about 35% (w/w), for example, about 20% to about 30% (w/w).

The D-psicose-containing solution produced as above is subjected to first cooling and ion purification. The first cooling refers to a process of reducing the solution temperature or ambient temperature to 25° C. to 45° C., specifically 30° C. to 40° C. In one embodiment, the mother liquor produced by D-psicose crystallization may be reused in first cooling and ion purification. Specifically, cooling may be performed such that the temperature is slowly lowered at a rate of 1° C. to 10° C. per hour through a heat exchanger. If D-psicose is continuously exposed to a certain temperature, D-psicose can be decomposed through heat deformation, thereby reducing D-psicose purity in the process flow of production. Accordingly, it is difficult to achieve high yield production of D-psicose (see FIGS. 4 to 8). Thus, according to the present invention, heat deformation of D-psicose is prevented by controlling temperature in each process of the method.

Next, ion purification refers to a purification process that allows the cooled solution to pass through a column filled with a strongly acidic cation exchange resin and/or a weakly basic anion exchange resin. If a strong basic anion resin is used, D-psicose can be deformed at a low temperature of 25° C. to 45° C., thereby causing deterioration in purity. Therefore, in order to produce D-psicose with high yield, a strongly acidic cation exchange resin or a weakly basic anion exchange resin may be used. More specifically, a 100% weakly basic anion exchange resin is used. A cation exchange resin and an anion exchange resin may be used at the same time in order to effectively remove ion components. In this case, the ratio of the cation exchange resin to the anion exchange resin may be 1:0.5 to 1:3. During ion purification, a temperature of 25° C. to 45° C., specifically 30° C. to 40° C. is maintained to prevent deformation of D-psicose. Accordingly, it is possible to remove ion components contained as contaminants in the D-psicose-containing solution. After ion purification, the content of ion components is 20 microsiemens or less, specifically 10 microsiemens per cm or less, as measured by a conductivity meter. D-psicose in the ion purified solution has a purity of about 10% (w/w) to about 35% (w/w).

Then, the ion purified D-psicose-containing solution is subjected to first concentration and second cooling.

The first concentration refers to a process of concentrating the ion purified D-psicose-containing solution such that the solution has a D-psicose concentration of 50 brix to 70 brix, for example, 55 brix to 65 brix. Specifically, it is possible to concentrate the ion purified D-psicose-containing solution at a temperature of 60° C. to 80° C., for example, 65° C. to 75° C. for 1 minute to 1 hour, specifically 1 minute to 30 minutes. For concentration, a low temperature evaporator may be used in order to prevent deformation of D-psicose. As used herein, the term, brix refers to weight percent of D-psicose or D-fructose based on the total weight of the solution. After first concentration, second cooling may be performed. When second cooling is performed, the solution temperature or ambient temperature may be reduced to a temperature lower by at least 10° C. than that of the first concentration. In one embodiment, the temperature for the second cooling may be 50° C. to 60° C. Specifically, temperature may be slowly reduced at a cooling rate of 5° C. to 25° C. per hour through a heat exchanger. In one embodiment, the mother liquor produced by D-psicose crystallization may be reused in the first concentration and/or second cooling.

Thereafter, the concentrated and cooled D-psicose-containing solution may be subjected to chromatography to obtain mother liquor and a D-psicose-containing separated solution.

The chromatography refers to a process of separating D-psicose by taking advantage of weak bonding strength between D-psicose and metallic ions attached to ion resins. For example, the chromatography may be continuous chromatography. Ion resins used in chromatography may be a strongly acidic cation exchange resin to which K, Na, Ca, or Ma residues are attached. In view of separation of D-psicose and D-fructose, K, Ca, or Na is advantageously used. By chromatography, it is possible to obtain a D-fructose-containing solution and a D-psicose-containing separated solution. The D-psicose-containing separated solution may be a D-psicose-containing fraction having a purity of 90% (w/w) or more, for example, 95% (w/w) or more. Specifically, D-psicose has a purity of 90 to 99% (w/w) or more.

The D-fructose-containing solution may be a D-fructose-containing fraction having a purity of 70% (w/w) or more. The D-fructose-containing solution may be reused in the epimerization of D-psicose. Prior to reuse, the method may further include cooling the solution to a temperature of 25° C. to 45° C., specifically 30° C. to 40° C.

Thereafter, the D-psicose-containing separated solution is subjected to second concentration and third cooling to obtain D-psicose crystals. The D-psicose solution separated by chromatography and having a purity of 90% (w/w) or more, for example, a purity of 95% (w/w) or more, is subjected to second concentration such that the separated solution has a D-psicose concentration of 75 brix or more, for example, 80 brix or more. Concentration is performed specifically at 60° C. to 80° C., for example, 65° C. to 75° C. for 1 minute to 1 hour, specifically for 1 minute to 30 minutes. For concentration, it is possible to use a low temperature evaporator in order to prevent deformation of D-psicose. After second concentration, third cooling may be performed. Third cooling serves to crystallize D-psicose, and may include reducing the solution temperature or ambient temperature to 30° C. to 40° C. More specifically, third cooling may be slowly performed such that the solution temperature or ambient temperature is reduced by 5° C. to 20° C. per hour to 25° C. to 45° C., for example, 30° C. to 40° C. Within the temperature range, heating and cooling may be repeatedly performed 5 times to 10 times for 40 hours to 120 hours in order to perform crystallization. The obtained D-psicose crystal may be further dehydrated and dried. The obtained D-psicose crystal may have a purity of 95% or more, specifically 99% or more. Further, the D-psicose crystal may have a yield of 75% or more, 80% or more, or 85% or more, as calculated in accordance with Equation 1:

Yield (%)=(Weight of dehydrated and dried D-psicose crystals/weight of D-psicose contained in solution to be crystallized)×100.

In calculation of the yield, the weight (g/L) of D-psicose contained in the solution to be crystallized is determined by HPLC (high performance liquid chromatography) analysis. Then, the measured value is substituted into Equation 1, thereby calculating the weight of D-psicose contained in a specific solution (L).

The mother liquor except for D-psicose crystals produced upon crystallization of D-psicose may be reused in each of the above processes. In one embodiment, the mother liquor produced upon crystallization may be reused in one or more processes selected from first cooling and ion purification, first concentration and second cooling, and chromatography processes. The mother liquor produced by D-psicose crystallization may be cooled to 25° C. to 45° C. and then reused. The mother liquor produced by D-psicose crystallization may be a D-psicose containing fraction having a purity of 90% (w/w) or more, a purity of 92% (w/w) or more, or a purity of 95% (w/w) or more.

Hereinafter, the present invention will be described in more detail with reference to some examples. It should be understood that these examples are provided for illustration only and are not to be construed in any way as limiting the present invention.

Descriptions of details apparent to those skilled in the art will be omitted herein.

EXAMPLES

Example 1

Crystalline fructose having a purity of 99% (w/w) or more, a mother liquor collected from continuous chromatography at about 30° C., a mother liquor collected from crystallization at about 30° C., and water at about 30° C. were mixed in a solution tank to prepare a substrate 50 brix (%) solution for enzyme reaction.

As disclosed in Korean Patent Application No. 10-2009-0118465, enzyme reaction was performed by immobilizing D-psicose epimerase separated from *Corynebacterium glutamicum* KCCM 11046 at sodium alginate as a carrier, followed by filling isomerization equipment (isomerization tower, manufactured by Hanju Machine Industry Inc.) with the immobilized enzyme, applying the prepared substrate solution for enzyme reaction to the isomerization tower, and heating the substrate solution at 5° C. to 20° C. per hour up to 50° C. through a heat exchanger such that SV [Space Velocity: flow rate (L)/hour (Hr)/resin amount (L)] became 0.5. Here, the resulting D-psicose had a purity of about 24% (w/w).

The D-psicose solution having a purity of 24% (w/w) was subjected to first cooling at a rate of 5° C. to 10° C. per hour down to a temperature of 30° C. to 40° C. through a heat exchanger, and was then passed through a column filled with a strongly acidic cation exchange resin substituted with hydrogen groups (Lewatit S 1668) and a column filled with a weakly basic anion exchange resin substituted with hydroxyl groups (Lewatit S 4528) such that SV [Space Velocity: flow rate (L)/hour (Hr)/resin amount (L)] became 3, thereby removing ion components remaining in the enzyme reaction solution. Removal of the ion components was measured using a conductivity meter. Here, conductivity was adjusted to not more than 10 microsiemens per cm, and the purity of D-psicose was maintained at 24% (w/w).

The ion purified D-psicose-containing solution was introduced into a low temperature evaporator (Forced Thin Film Evaporator, Welcronhantec Co., Ltd.), concentrated to 60 brix (%) (D-psicose solution×100/total solution) at 65° C. to 75° C. for a short period of time from 10 minutes to 15 minutes. The resulting solution was subjected to second cooling at a rate of 5° C. to 25° C. per hour through a heat exchanger, and was then passed through a column filled with a strongly acidic cation exchange resin with calcium active groups attached thereto at 50° C. to 60° C. Through such continuous chromatography, a fraction containing D-psicose having a purity of 95% (w/w) or more and a fraction containing D-fructose having a purity of 75% (w/w) or more were separated.

The mother liquor separated through continuous chromatography, namely, the D-fructose fraction having a purity of 75% (w/w) or more, was collected and cooled at a rate of 20° C. to 30° C. per hour. When the fraction reached 30° C., the fraction was re-circulated to an enzyme reaction process.

The D-psicose solution having a purity of 95% (w/w) or more separated through continuous chromatography was concentrated to 80 brix (%) at 65° C. to 75° C. in a short period of time from 10 minutes to 15 minutes. The concentrated D-psicose solution having a purity of 95% (w/w) or more was rapidly cooled to 40° C. at a rate of 5° C. to 20° C. per hour through a heat exchanger. The heating and cooling were repeated 5 times to 10 times within the temperature range from 35° C. to 40° C. such that crystallization was performed for 80 hours to 120 hours, thereby obtaining D-psicose (see FIG. 1). In addition, the mother liquor separated through crystallization, namely, a D-psicose fraction having a purity of 90% or more, was collected, cooled to 30° C., and passed through a column filled with a strongly acidic cation exchange resin substituted with hydrogen groups and a column filled with a weakly basic anion exchange resin substituted with hydroxyl groups.

Through the above procedures, the D-psicose solution was concentrated for a short period of time in a low temperature evaporator while the process temperature was adjusted to a low temperature through the heat exchanger, thereby obtaining a high purity D-psicose having a purity of 99% or more with outstanding yield of 75% or more.

Comparative Example 1

High purity D-psicose having a purity of 99% or more was produced by the same method as in Example 1 wherein the D-fructose-containing mother liquor produced in the continuous chromatography was reused in D-psicose epimerization and the mother liquor produced through the D-psicose crystallization was reused, except that cooling procedures including first cooling and second cooling were omitted. The production yield was 60%.

Purity of D-psicose is reduced in a certain concentration or less and after a certain period of time (see FIGS. 4 to 8). Thus, if the D-fructose mother liquor separated through continuous chromatography and the mother liquor separated through crystallization are continuously re-circulated without cooling, the purity of D-psicose introduced to continuous chromatography will be decreased from an initial purity of 24% (w/w) in proportion to repeated times of re-circulation, and yield of a high purity D-psicose fraction having a purity of 95% (w/w) or more to be crystallized will also be reduced. Thus, it is considered that such low yield of high purity D-psicose fraction having a purity of 95% (w/w) or more acts as a cause of decrease in production yield of high purity D-psicose having a purity of 99% or more. Moreover, deformed impurities derived from D-piscose are separated as a D-fructose fraction in the course of continuous chromatography separation, thereby causing problems in continuous chromatographic separation as re-circulation times are accumulated. In order to control such impurity accumulation, about 5% (v/v) to 10% (v/v) of the D-fructose fraction is discarded, thereby causing decrease in production yield of high purity D-psicose having a purity of 99% or more.

If about 5% (v/v) to 10% (v/v) of the D-fructose mother liquor separated through continuous chromatography is not discarded, the purity of D-psicose introduced to continuous chromatography will be continuously decreased due to accumulated impurities. Therefore, in order to separate high purity D-psicose having a purity of 95% (w/w) or more, separation conditions for continuous chromatography must be continuously modified, thereby causing deterioration in industrial production efficiency. Further, in order to separate high purity D-psicose having a purity of 95% (w/w) or more, the amount of de-ionized water is also increased, thereby causing burdens on the concentration process. As a result, a bottleneck phenomenon occurs in a process flow, thereby causing decrease in production amount and increase in production costs.

Comparative Example 2

Figure 3:
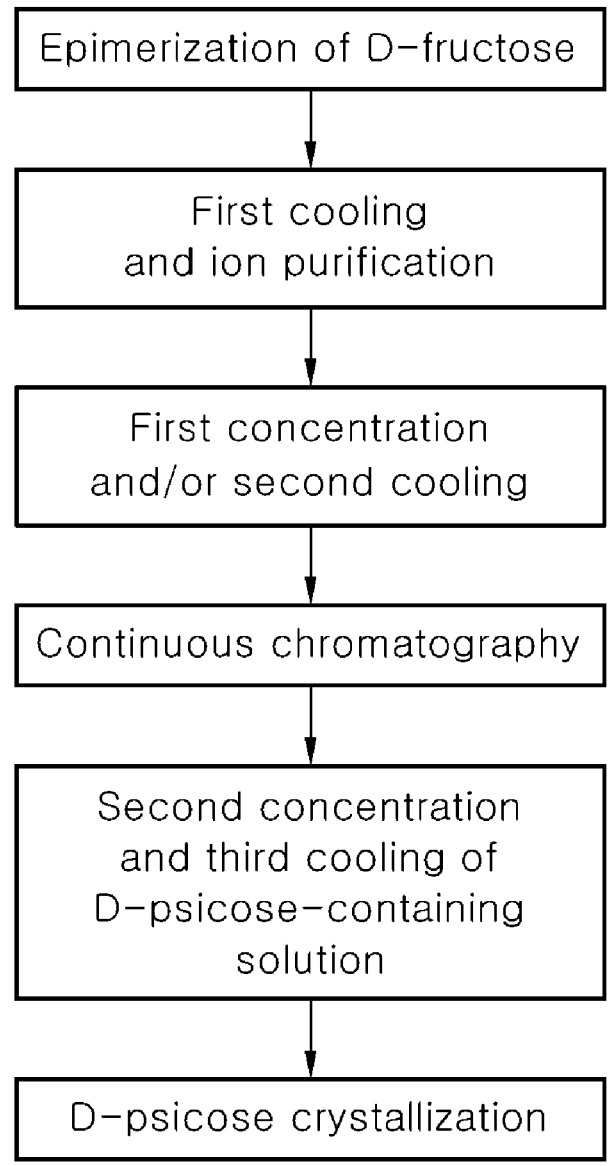
FIG. 3 is a schematic view depicting a method of producing D-psicose according to Comparative Example 2.
Figure 4:
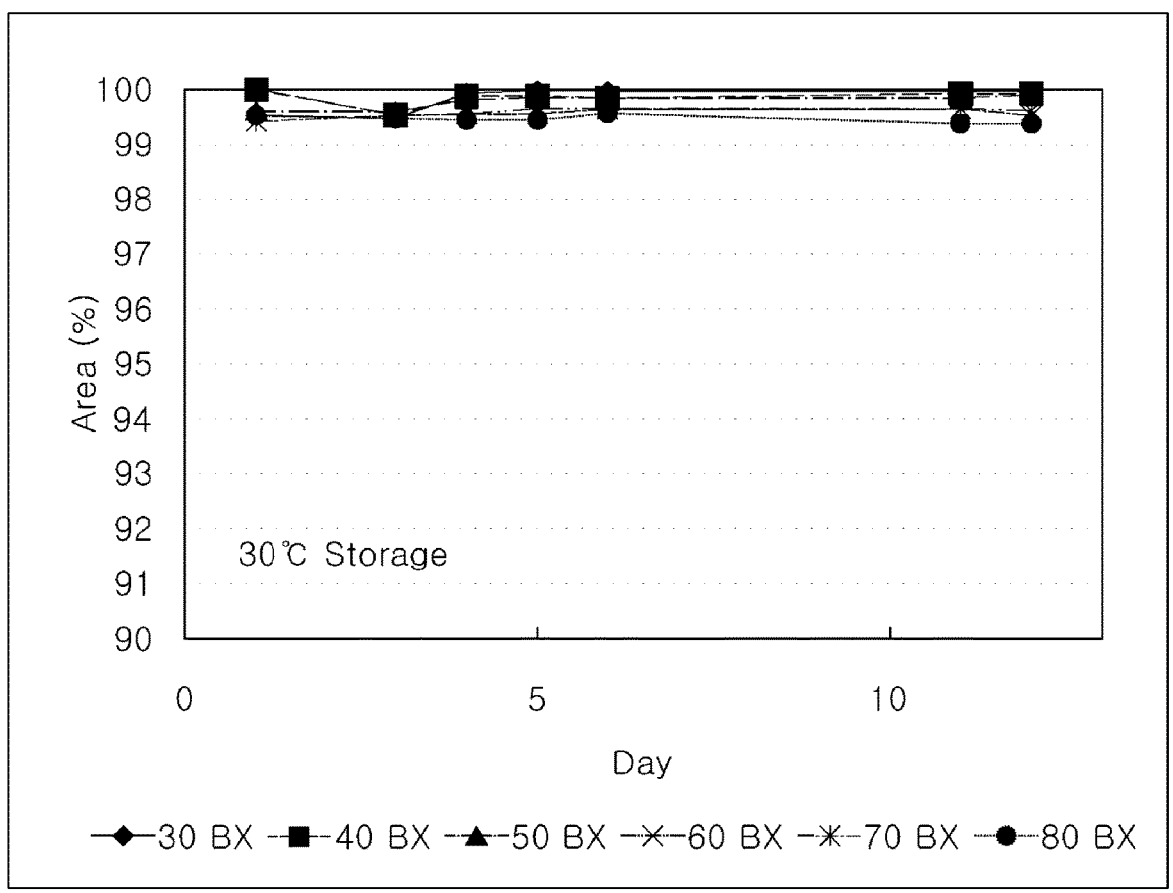
FIGS. 4 to 8 show graphs depicting changes in purity % (w/w) of D-psicose depending on temperature and concentration of D-psicose.
Figure 5:
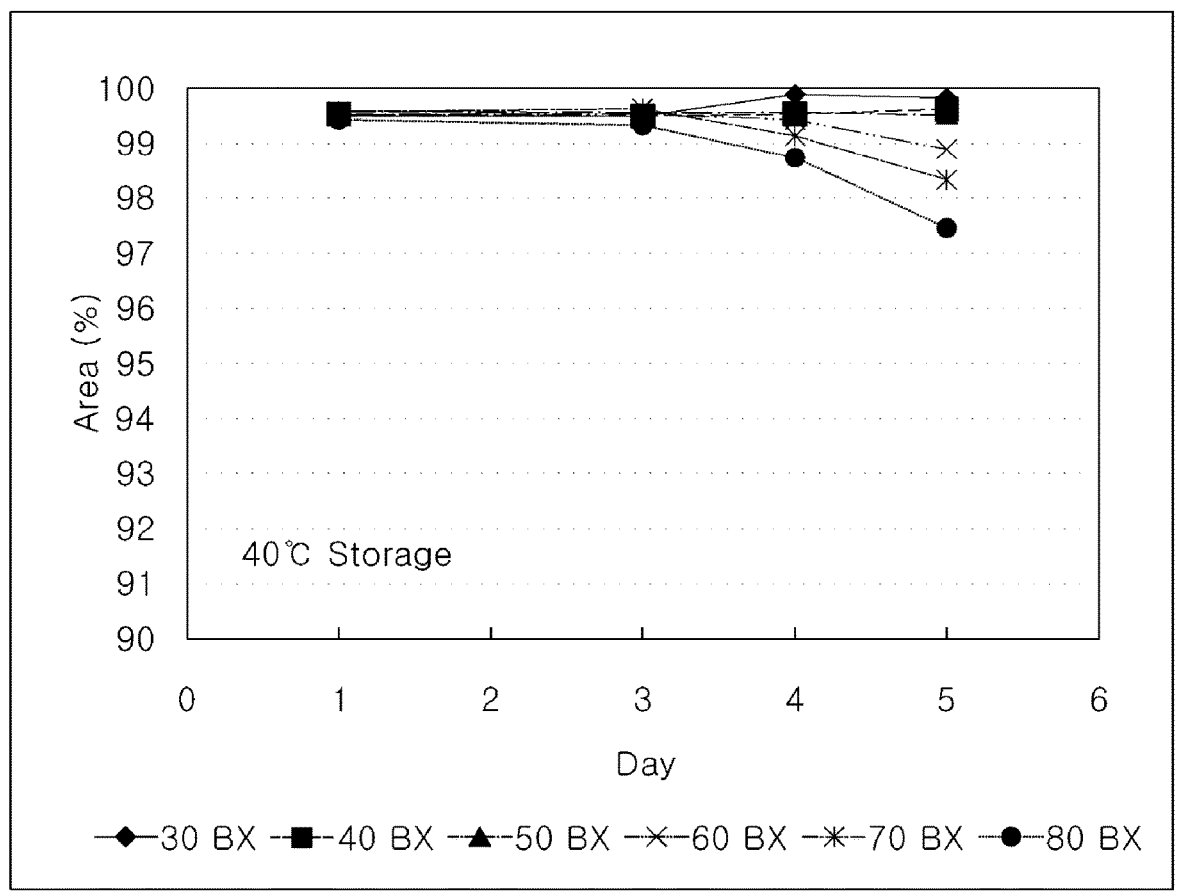
Figure 6:
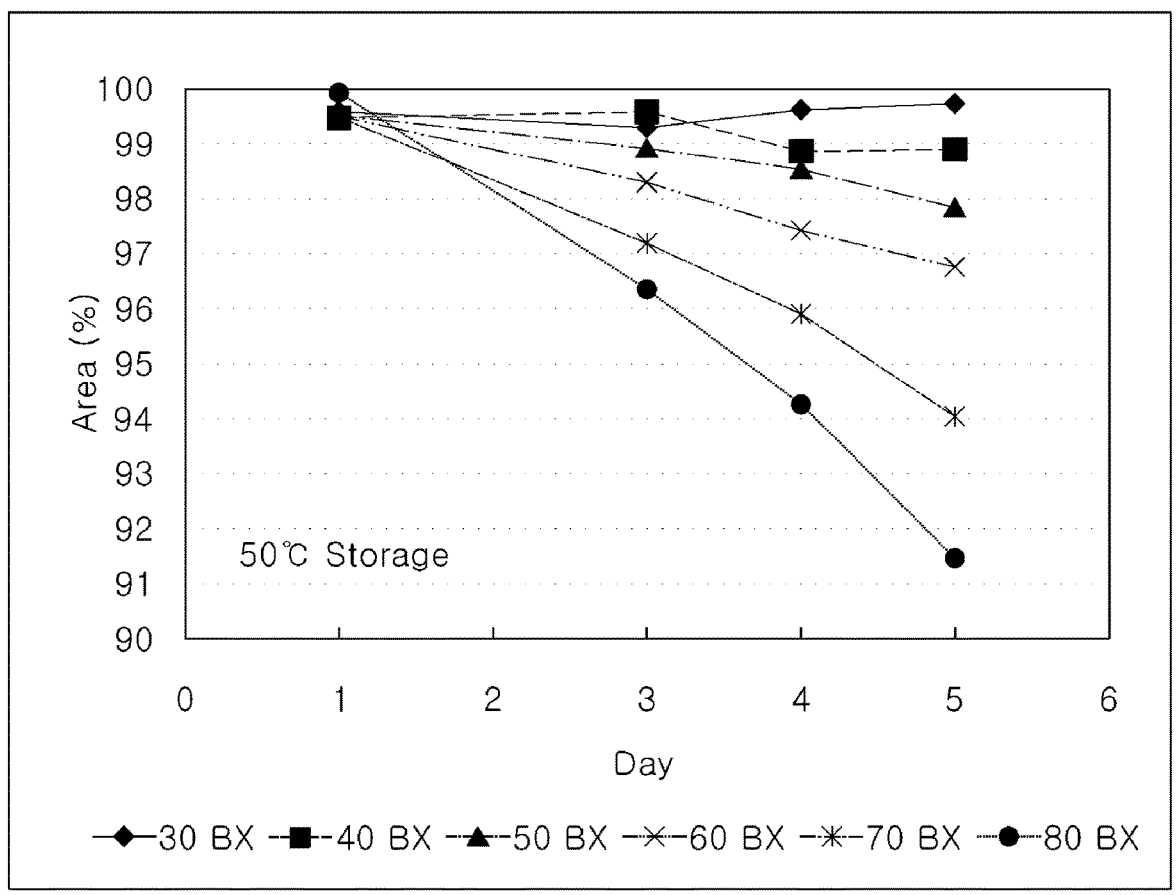
Figure 7:
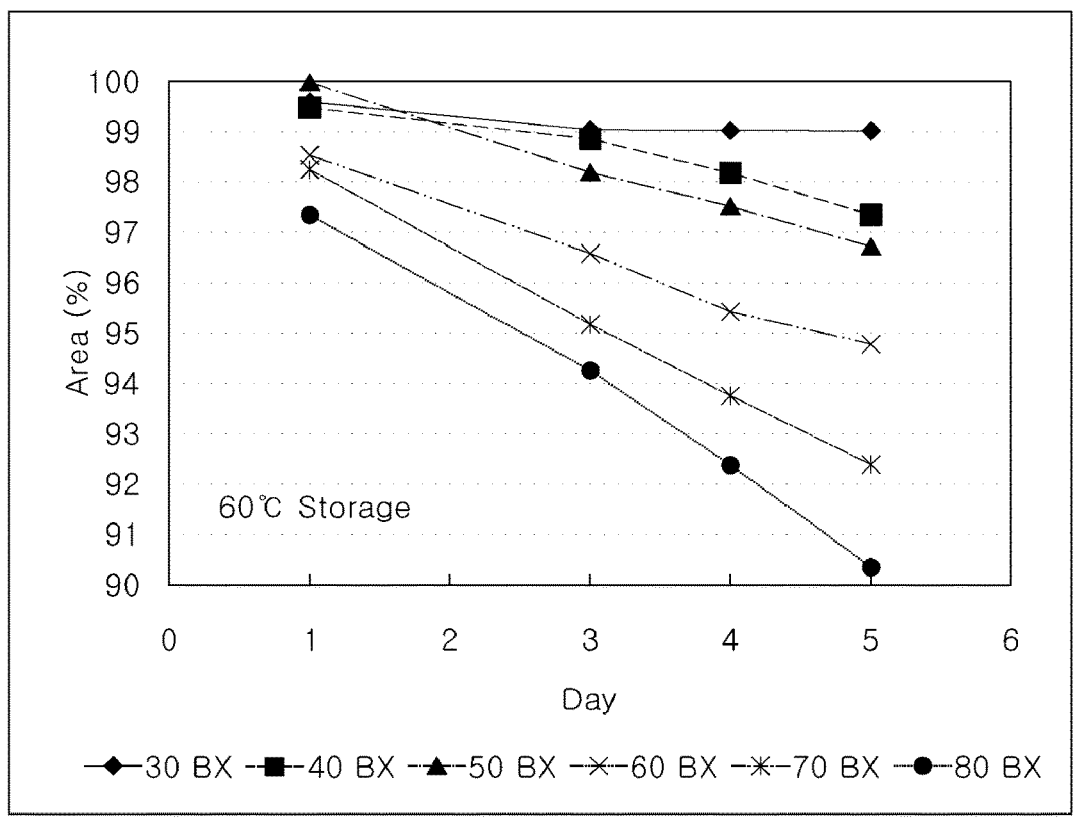
Figure 8:
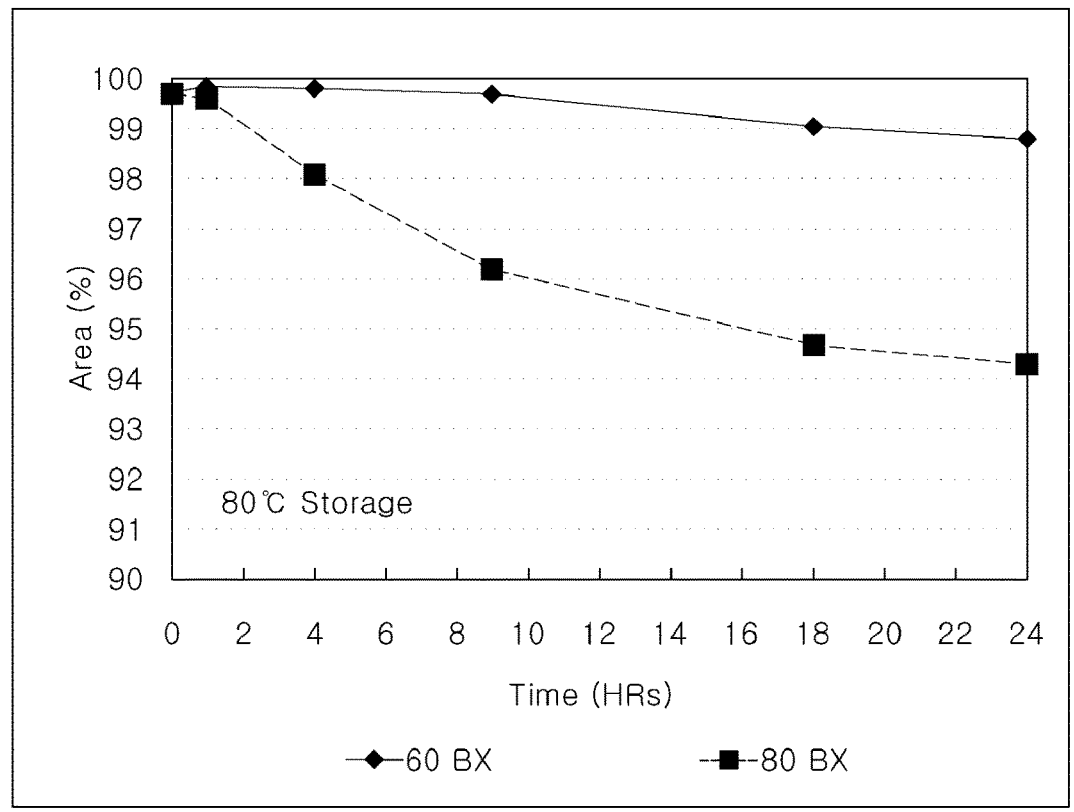

High purity D-psicose having a purity of 99% or more was produced by the same method as in Example 1 except that re-use of the D-fructose-containing mother liquor produced though continuous chromatography in D-psicose epimerization and re-use of the mother liquor produced through D-psicose crystallization were omitted. The production yield was 20% (see FIG. 3).

Although some embodiments have been described herein, it should be understood that these embodiments are given by way of illustration only, and that various modifications, variations, and alterations can be made by those skilled in the art without departing from the spirit and scope of the invention. Therefore, the scope of the invention should be limited only by the appended claims and equivalents thereof.

What is claimed is:
1. A method of producing D-psicose, comprising:
subjecting D-fructose to D-psicose epimerization to produce a D-psicose-containing solution,
subjecting the D-psicose-containing solution to first cooling and ion exchange purification,
subjecting the purified D-psicose-containing solution to first concentration and second cooling,
subjecting the D-psicose-containing solution, which has been subjected to first concentration and second cooling, to chromatography to obtain a D-fructose-containing mother liquor and a D-psicose-containing separated solution, and
subjecting the D-psicose-containing separated solution to second concentration and third cooling to crystallize D-psicose and thereby obtaining D-psicose crystals produced through D-psicose crystallization and a mother liquor containing a remaining D-psicose, wherein the D-fructose-containing mother liquor produced by chromatography is reused in the D-psicose epimerization, and
wherein the mother liquor containing the remaining D-psicose is reused in the first cooling and ion purification, the first concentration and second cooling, or the chromatography.

2. The method of producing D-psicose according to claim 1, wherein the mother liquor produced containing the remaining D-psicose is reused in the first cooling and ion exchange purification.

3. The method of producing D-psicose according to claim 1, wherein the chromatography is continuous chromatography.

4. The method of producing D-psicose according to claim 1, wherein the D-fructose-containing mother liquor produced by the chromatography or the mother liquor containing the remaining D-psicose is cooled to 25° C. to 45° C. before reusing.

5. The method of producing D-psicose according to claim 1, wherein the first cooling and the third cooling are performed by cooling the solution temperature or ambient temperature to 25° C. to 45° C., and the second cooling is performed by lowering the solution temperature or ambient temperature to 45° C. to 65° C.

6. The method of producing D-psicose according to claim 5, wherein the first cooling and the third cooling are performed by cooling solution temperature or ambient temperature to 30° C. to 40° C., and the second cooling is performed by lowering solution temperature or ambient temperature to 50° C. to 60° C.

7. The method of producing D-psicose according to claim 1, wherein the first concentration is performed such that the purified D-psicose-containing solution has a D-psicose concentration of 50 brix to 70 brix, and the second concentration is performed such that the separated solution has a D-psicose concentration of 75 brix or more.

8. The method of producing D-psicose according to claim 1, wherein the D-fructose-containing mother liquor produced by the chromatography is a D-fructose-containing fraction having a purity of 70% (w/w) or more.

9. The method of producing D-psicose according to claim 1, wherein the mother liquor produced by the D-psicose crystallization is a D-psicose-containing fraction having a purity of 90% (w/w) or more.

10. The method of producing D-psicose according to claim 1, wherein the D-psicose epimerization is performed at 40° C. to 70° C. in the presence of D-psicose epimerase, variants thereof, strains capable of producing the enzyme or cultures thereof.

11. The method of producing D-psicose according to claim 1, wherein the ion exchange purification employs a strongly acidic cation exchange resin or a weakly basic anion exchange resin.

12. The method of producing D-psicose according to claim 1, wherein the D-psicose-containing separated solution comprises D-psicose having a purity of 93% (w/w) or more.

13. The method of producing D-psicose according to claim 1, wherein any one or more of the first cooling to the third cooling are heat exchange cooling.

14. The method of producing D-psicose according to claim 1, wherein the obtained D-psicose crystal has a purity of 95% or more.

15. The method of producing D-psicose according to claim 14, wherein the obtained D-psicose crystal has a purity of 99% or more.

16. The method of producing D-psicose according to claim 1, wherein the D-psicose crystal has a yield of 75% or more.

\* \* \* \* \*